United States Patent [19]

Folkman et al.

[11] 4,164,560

[45] Aug. 14, 1979

[54] SYSTEMS FOR THE CONTROLLED RELEASE OF MACROMOLECULES

[76] Inventors: Moses J. Folkman, 18 Chathman Cir., Brookline, Mass. 02146; Robert S. Langer, Jr., 1200 Commonwealth, Apt. 2, Allston, Mass. 02134

[21] Appl. No.: 756,892

[22] Filed: Jan. 5, 1977

[51] Int. Cl.$^2$ .................. A61K 9/26; A61K 37/26
[52] U.S. Cl. ...................... 424/22; 128/260; 424/19
[58] Field of Search ................. 424/19–22, 424/78–83; 128/260; 195/163

[56] References Cited

U.S. PATENT DOCUMENTS

| | | | |
|---|---|---|---|
| 3,854,480 | 12/1974 | Zaffaroni | 128/260 |
| 3,880,991 | 4/1975 | Yolles | 424/22 |
| 3,903,880 | 9/1975 | Higuchi et al. | 128/130 |
| 3,957,740 | 5/1976 | Blank et al. | 526/16 |
| 4,016,251 | 4/1977 | Higuchi et al. | 424/15 |
| 4,052,505 | 10/1977 | Higuchi et al. | 424/14 |
| 4,057,619 | 11/1977 | Higuchi et al. | 424/14 |
| 4,069,307 | 1/1978 | Higuchi et al. | 424/22 |

FOREIGN PATENT DOCUMENTS 76-32785 3/1976 Japan.
1388580 3/1975 United Kingdom.
1443662 7/1976 United Kingdom.

OTHER PUBLICATIONS

Chem. Abstracts 85 #42991j (1976) of Japan Kokai 76 32,785 19 Mar. 1976, Kuraray—"Immobilized Enzymes Entrapped in Ethylene-Vinylacetate-Vinyl Alcohol Copolymers".
Chem. Abstracts 86 #13233d, #13234b, #13237h, #91290j, #67536y, #67983s, #116803u (1977).
Chem. Abstracts 82 #21790r (1975) of Davis, B. K. Proc. Natl. Acad. Sci. U.S.A. (1974), 71(8): 3120-3, "Diffusion in Polymer Gel Implants".
Chem. Abstracts 77 #14570n (1972) of Davis, B. K. by Perientia (1972) 28(3) 348 "Control of Diabetes with Poly Acrylamide Implants Containing Insulin".

*Primary Examiner*—Shep K. Rose

[57] ABSTRACT

Delivery systems manufactured in the form of polymeric compositions for the controlled delivery of macromolecules to environments of use are disclosed. The systems are characterized as two-phase compositions comprising a phase formed of an insoluble polymeric matrix having limited water sorptivity containing in admixture therein an interpenetrating phase formed of a particulate hydrophilic water swellable, biologically active macromolecular material.

12 Claims, 2 Drawing Figures

SYSTEMS FOR THE CONTROLLED RELEASE OF MACROMOLECULES

The invention described herein was made with partial support provided from a grant or award from the Department of Health, Education and Welfare.

FIELD OF THE INVENTION

This invention relates to both novel and useful systems for delivering macromolecules. More particularly, the invention pertains to systems in the form of polymeric compositions useful for the controlled and continuous delivery of water swellable, biologically active macromolecules from a polymer matrix having limited water sorptivity over prolonged periods of time.

BACKGROUND OF THE INVENTION

In recent years, much research has been done in developing systems using polymeric compositions for the programmed release of active agents, especially drugs, over periods of time. The purpose of these systems is to dispense the agent at a controlled, and if desired, constant rate in order, as in the case of pharmaceutical agents or drugs, to improve therapy by presenting the drug in the most beneficial and reliable manner, with a minimum possibility of complications from the drug or from failure to comply with the therapeutic regimen. For example, see Folkman, et al., in *Journal of Surgical Research*, Vol. 4, pages 139 to 142, 1964; U.S. Pat. No. 3,832,252 issued to Higuchi, et al.; and U.S. Pat. No. 3,854,480 issued to Zaffaroni. Both of these patents are assigned to the Alza Corporation of Palo Alto, Calif.

While the above systems represent an extraordinary advancement in the art, and while they possess ideal kinetics for effectively delivering low molecular weight agents, a limiting feature associated with these systems is they are not designed to deliver agents which possess macromolecular structures. This is so since such systems operate, in the case where the polymer matrix is not absorbable in the environment, by diffusion which fundamentally depends on the agent permeating at a controlled rate through the polymer. Inasmuch as macromolecular agents do not diffuse through polymeric materials at rates which are high enough to be used to advantage, these prior art systems cannot be used satisfactorily for delivering macromolecular agents. It is also disclosed in U.S. Pat. Nos. 3,896,819 and 3,948,254, issued to Zaffaroni and assigned to the ALZA Corp., that certain large molecules can be released by the delivery devices as defined therein; however, the devices of these patents are structurally distinct, operate differently, and accordingly they do not provide the beneficial release kinetics as obtained with the system of this invention.

It is apparent from the foregoing presentation that a critical need exists for systems that can successfully deliver macromolecular agents. The prior art has made systems that seemingly attempted to satisfy this need, but the results obtained has not lead to acceptable application of the systems. For example, Davis in the "Control of Diabetes With Polyacrylamide Implants Containing Insulin," *Experientia*, Vol. 28, page 348, 1972, and in "Diffusion in Polymer Gel Implants," *Proc. Nat. Acad. Sci. USA*, Vol. 71, pages 3120 to 3123, 1974 disclosed gels formed of crosslinked, hydrophilic polyacrylamide and polyvinylpyrrolidone polymers containing protein solutes used as implants that release the solutes by simple diffusion over a limited period of time. However, these single phase gel compositions did not lead to systems having acceptable release properties because the duration of release depends on the density of the gel which property is difficult to control with standard manufacturing techniques, and also because the rate of solute release follows an exponential time course until depletion of the solute is virtually complete. Similar attempts to release macromolecules were disclosed by Gimbrone, et al., in "Tumor Growth and Neovascularization: An Experimental Model Using the Rabbit Cornea," in *J. Nat. Can. Inst.*, Vol. 52, pages 413 to 427, 1974, with the use of polyacrylamide gels for delivering tumor angiogenesis factor, and by Gould, et al, in U.S. Pat. No. 3,576,760. In the patent, Gould, et al, disclosed the entrapment of enzymes in water soluble acrylic polymers which compositions release the enzyme upon contact with water by virtue of dissolution of the water soluble polymer. None of the prior art references has lead to an acceptable system for releasing macromolecular structures, particularly biologically active molecules of increased size and weight at controlled rates over prolonged periods of time.

OBJECT OF THE INVENTION

Accordingly, it is an object of the present invention to provide both novel and useful systems for delivering macromolecular structures at controlled rates over prolonged periods of time to environments of use to produce a desired result.

Another object of the invention is to provide a therapeutic system that can be simply manufactured suitable for delivering very potent biologically active proteins and polypeptides at controlled and substantially constant low rates over prolonged periods of time.

Other objects and features of the invention will be more apparent to those versed in the art from the detailed description of this specification, taken in conjunction with the tables and the accompanying claims.

SUMMARY OF THE INVENTION

This invention resides on the discovery that certain biologically active macromolecules may be delivered in a controlled and continuous manner using substantially insoluble polymer matrixes of limited aqueous and biological fluid sorptivity over prolonged periods of time. The systems are defined as a body which is sized, shaped and adapted for placement and retention in the environment of use, comprising a two-phase composition of:

(A) A biocompatible plastically deformable polymer matrix of fluid sorptivity not greater 50% by weight, the polymer being insoluble in the environment of use, substantially impermeable to a macromolecule, and containing in admixture therewith;

(B) From about 3 parts to 90 parts by weight of an interpenetrating phase comprising a particulate hydrophilic fluid swellable, biologically active macromolecular material having a molecular weight of at least 1000; and, wherein when the system is placed in the environment, fluid is absorbed by the biologically active macromolecular phase causing such phase to swell and exert pressure on the matrix, whereby the biologically active macromolecule is released from the matrix at a controlled and continuous rate over a prolonged period of time.

DETAILED DESCRIPTION OF THE INVENTION

Figure 1:
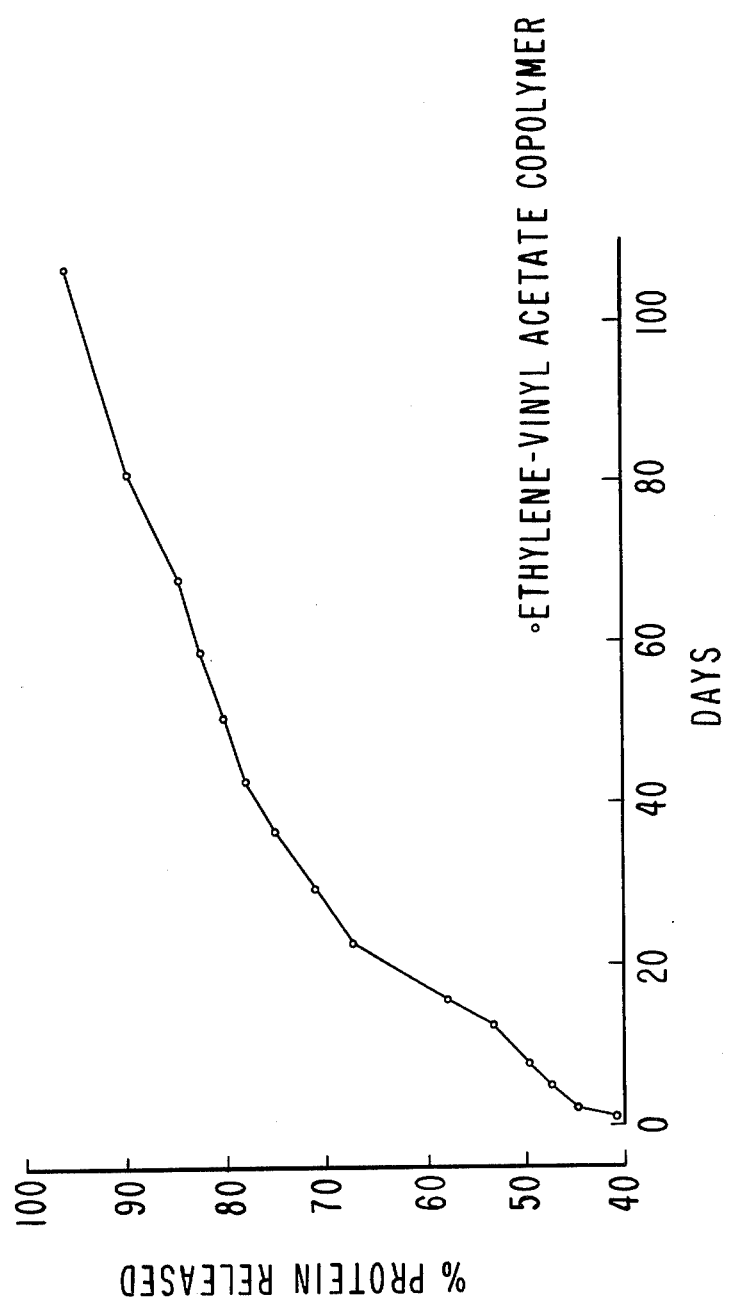

It should be understood that the detailed description and specific examples, while indicating preferred embodiments of the invention, are given by way of illustration only, since various changes and modifications within the spirit and scope of the invention will become apparent to those skilled in the art from this description and the accompanying claims.

The term "matrix" as used herein denotes a carrier polymeric phase for the interpenetrating phase with the matrix comprising a polymer that is biocompatible and sufficiently resistant to chemical and/or physical attack by the environment of use, such that the matrix remains substantially intact throughout the prolonged period of time the macromolecule is released from the system.

The polymer matrixes, which are suitably used in the present invention, are biocompatible in the environment of use, plastically deformable, have limited water sorptivity, and they are substantially impermeable to the passage of biologically active macromolecular materials in admixture therewith. Additionally, while the amount of water sorption needed to obtain optimum release varies with the specific polymer matrix, generally the useful and preferred polymers suitable for forming the matrix will absorb a maximum of not greater than about 50% by weight of water to form the system and obtain the desired macromolecular release properties. Preferably, the sorptivity of the polymer matrix is between 30% and 50% by weight of water and in a still more preferred embodiment the sorptivity of the polymer matrix is less than 30% by weight of water. The term "water" as used herein includes biological fluids, saline and physiologically acceptable buffer.

Typical polymeric material suitable for forming the matrix and having the above described water sorption, expressed as a weight percentage of the initial dry weight at the temperature of use, are the naturally occurring and synthetic commercially available polymers. They include acyl substituted cellulose acetates and alkyl derivatives thereof; partially and completely hydrolyzed alkylene-vinyl acetate copolymers; unplasticized polyvinyl chloride; crosslinked homo- and copolymers of polyvinyl acetate; crosslinked polyesters of acrylic and methacrylate; polyvinyl alkyl ethers; polyvinyl fluoride; silicone; polycarbonate; polyurethane; polyamide; polysulphones; styrene acrylonitrile copolymers; crosslinked poly(ethylene oxide); poly(alkylenes); poly(vinyl imidazole); poly(esters); poly(ethylene terephthalate); and chlorosulphonated polyolefins.

In a presently preferred embodiment the polymeric materials useful for forming the matrix are the ethylenevinyl ester copolymers of the general formula:

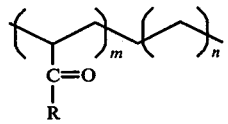

wherein R is hydrogen, lower alkyl of 1 to 7 carbons and aryl, and m is (10 to 40)% by weight and n is (100 -m)% by weight. Typical alkyl groups include ethyl, propyl, isopropyl, tert-butyl, pentyl, and hexyl. Typical aryl groups include phenyl. Representative ethylene-vinyl ester copolymers suitable for forming the matrix, with the copolymers named as the acetates, include ethylene-vinyl acetate, ethylene-vinyl methylacetate, ethylene-vinyl ethylacetate, ethylene-vinyl propylacetate, and the like. In its broadest aspects, the present invention contemplates the use of ethylene-vinyl ester copolymers having a melt index of about 0.5 to 100 grams per ten minutes, a density of 0.920 to 1.00, and a frequency of acyl, for example acetoxy groups, on the polyethylene backbone of 1/70 to ½. In a preferred embodiment, the copolymer is ethylenevinyl acetate having a vinyl acetate content of about 10 to 50% by weight, a melt index of about 0.5 to 250 grams per ten minutes, a density having a range of about 0.920 to 0.980, and a frequency of acetoxy groups on the polyethylene backbone of 1/70 to ½. Typical water sorptivities for ethylene-vinyl acetate copolymers having a vinyl content of 10%, 30% and 40% are 0.015%, 0.25%, and 0.67% respectively. The ethylene-vinyl ester copolymers are known, commercially available materials and exemplary techniques for their preparations are described in U.S. Pat. Nos. 2,200,429, 2,396,785, and 2,947,735, in British Pat. Nos. 569,927 and 582,093, and in *Crystalline Olefin Polymers*, Edited by Raff, R. A. V., and Doak, V. W., Part II, pages 261 to 266, 1964, published by Interscience Publishers Inc., New York.

The biologically active macromolecules that can be suitably employed in accordance with the invention with warm blooded animals including humans, veterinary animals, and farm animals, are macromolecules that are swellable in water and biological fluids and have a molecular weight of at least 1000. Exemplary macromolecules include proteins such as the peptide hormones that circulate in the blood of warm blooded animals such as insulin, glucagon, parathyroid and pituitary hormones, calcitonin, vasopressin, renin, prolactin, growth hormone, thyroid stimulating hormone, corticotrophin, follicle stimulating hormone, luteinising hormone and chorionic gonadotrophin. These hormones, with their molecular weights ranging from 1,010 to 36,700, and their specific activity are reported in *Peptide Hormones*, Edited by Parsons, J. A., Forward Section, 1975, published by University Park Press, London. Other macromolecules include the physiologically active enzymes transfereses, hydrolases, lysases, isomerases, protease, ligases, and oxidoreductases such as esterases, phosophatases, glycosidases and peptidases as disclosed in *Enzymes*, edited by Dixon M. and Webb, E. C., 1964, published by Academic Press Inc., New York, and the enzyme inhibitors such as leupeptin, antipain, chymostatin and pepstatin as reported in *Enzyme Inhibitors of Microbial Orgin*, by Umezawa, H., 1972 published by University Park Press, Tokyo. Other macromolecules within the molecular weight range of $10^3$ to $10^6$ daltons suitable for release according to the invention include, wherein M.W. is molecular weight, soybean trypsin inhibitor (M.W. 21,000), for example aprotinin, lysozyme (M.W. 14,000), catalase (M.W. 250,000), alkaline phosphatases (M.W. 88,000), tumor angiogenesis factor, cartilage factor (M.W. 16,000), and similar proteins as disclosed in *The Encyclopedia of Chemistry*, Second Edition, edited by Clark, G. L., and Hawley, G. G., pages 392 to 393 and 888 to 893, 1966, published by Van Nostrand Reinhold Company, New York, and in *Pharmaceutical Sciences*, by Remington, 14th Ed., pages 1426 to 1446, 1970, published by Mack Publishing Company, Easton, Pa.

The relative proportions of the biologically active macromolecule incorporated into the matrix to form the two-phase system, can be varied over a wide range depending on the macromolecule to be administered and the desired effect. Generally, the macromolecule can be present in an amount which will be released over controlled periods of time according to predetermined desired rates. This necessarily implies a quantity of macromolecule greater than the standard single dosage. Proportions suitable for the purpose of the invention can range from 3 to 90 parts by weight of macromolecule to 97 to 10 parts by weight of polymeric matrix. A preferred ratio includes 15 parts by weight of macromolecule formulated with sufficient polymeric matrix to give 100 parts by weight of system. A more preferred embodiment comprises 25 to 80 parts by weight of macromolecule mixed with up to 100 parts by weight of a polymeric matrix which forms the two-phase system of the invention.

The expression, "limited water sorptivity of the polymer matrix," as used herein is important as it denotes the ability of a selected polymer to function for the system of this invention. One procedure for determining water absorption of a given polymer comprises immersing a dry, measured section of polymer in water at 20° C. for 24 hours, and after its removal from water reweighing the polymer and expressing the gain in weight, as percent by weight of polymer, of water absorbed. Detailed procedures for measuring the water sorptivity of polymers are described in the *Handbook of Common Polymers*, Edited by Scott, J. R., and Roff, W. J., Section 61, 1971, published by Chemical Rubber Press, Cleveland, Ohio; by Daynes, H. A., in *Trans. Faraday Soc.*, Vol. 33, pages 531 to 544, 1933; in *Polymer Handbook*, Edited by Brandrup, J., and Immergut, E. H., Sections VI-33 and 88, 1967, published by Interscience Publishers, Inc. New York; and according to ASTM Section D-570.

The term "swellable" as used herein denotes a functionality of a macromolecule to expand or increase in physical size in the presence of swelling agents, mainly aqueous type fluids such as water and biological fluids. One procedure for measuring the swellability or the rate of swelling of a macromolecule comprises placing a known sample in the environment of a swelling agent at a known temperature and for a given time, then, after removing the sample from the environment measuring its change in dimensions followed by drying it and measuring it in the dry state. A method for determining swelling is disclosed in *Coll. Czech, Chem. Commun.*, Vol 34, pages 349 to 353, 1969, and the references cited therein; and in *Polymer Chemistry*, by Vollmert, B., pages 547 to 548, 1973, published by Springer-Verlag, New York.

The expression melt index as used herein denotes the number of grams of copolymer which can be forced through a standard cylindrical orifice under a standard pressure at a standard temperature and thus it is inversely related to the molecular weight. As used in this specification and the appended claims, melt index is as determined in accordance with standard ASTM D-1238-65T condition E practice.

In accordance with the present invention macromolecules are released at a controlled and continuous rate over a prolonged period of time. While not being bound by any particular theory, what makes the mechanism of release of macromolecules from the polymer matrix noteworthy and unexpected is that it cannot be explained by traditional concepts of diffusion. When the systems of this invention are placed in an aqueous environment, water will permeate by diffusion into the polymer matrix and be absorbed by the biologically active macromolecules. Since the macromolecules in question are ultimately molecularly dispersible in water, the dispersed particles will tend to swell as they absorb water. Since, however, the polymer matrix with which they are surrounded has little water-sorptivity, the swelling process is retarded by tensile stresses in the matrix. Nonetheless, the swelling pressure induced by the macromolecules causes gradual creep and relaxation of the matrix, allowing the particles to slowly sorb increasing amounts of water and increase in volume. Ultimately, a gelatinous, highly concentrated macromolecule solution will create channels or micropores in the matrix directly communicating with the external environment.

Then, residual stress in the plastically deformable matrix will tend to express gel-like macromolecule concentrate with bulk-flow delivery. Once this process has ceased, there can be further slow imbibition and swelling of the residual macromolecular gel, with further expulsion of macromolecules, and ultimately, when the residual macromolecular gel remaining in the pore spaces becomes sufficiently diluted to permit free diffusion of macromolecules, the macromolecules will be released by molecular diffusion through water within the pore spaces of the matrix. Since diffusion coefficients for macromolecules in water are very low, of the order of $10^{-7}$–$10^{-9}$ cm$^2$/sec, such systems may be expected to release at very low rates over very long time periods, as is observed. While zero-order release behavior is limited for these kinds of systems, they are nonetheless very useful for delivery of very potent substances at very low rates over very long time periods.

The systems of this invention can be manufactured in the form of delivery systems shaped as devices that can take a wide variety of shapes, sizes and forms for delivering numerous active and beneficial macromolecules to different environments of use. For example, the systems can be made as devices including buccal and oral devices; vaginal and intrauterine devices of cylindrical, bullet, elliptical, circular, bulbous, loop, bow or any other shape that lends itself to placement in these biological environments; the devices also include ocular devices of any geometric shape for comfortable placement in the cul-de-sac such as ellipsoid, bean, banana, circular, rectangular, doughnut, crescent, and half ring shaped devices. In cross-section the ocular devices can be doubly convex, concavo-convex, and the like. The dimensions of the ocular devices can vary according to the size of eye, with satisfactory eye devices generally having a length of 4 to 20 millimeters, a width of 1 to 15 millimeters and a thickness of 0.1 to 4 millimeters. Other devices made according to the spirit of the invention include implants, anal, pessaries and prosthestic devices, artificial glands for dispensing a pharmaceutically acceptable macromolecular agent having a physiological function essentially equivalent to a corresponding natural gland, cervical, nasal, ear and skin devices.

The two-phase systems of the invention can be manufactured into the above-described therapeutic systems for delivering a physiologically or pharmacologically active macromolecule that produces a localized or systemic effect or effects in animals, including warm blooded animals, humans and primates, sport and farm animals such as sheep, goats, cattle, horses and pigs, for administering to laboratory animals such as mice, rats ang guinea pigs, and to avians, fish, reptiles and zoo animals. The amount of macromolecular agent present in a two-phase delivery system is, in one embodiment, an amount initially in excess of the amount needed to satisfy the required dosage regimen over a prolonged period of time, for example up to three, or six months, one year, three years or the like. Generally, the system can house from 0.01 nanograms to 5 grams or more, with individual therapeutic delivery systems containing from 0.1 micrograms to 100 milligrams, 250 milligrams, 500 milligrams, 1 gram, 1.5 grams, and the like.

The two-phase systems of the invention, with the systems designed in the form of devices, are manufactured by standard techniques, provided, as is important to the invention, that such manufacture include process steps such as blending, mixing or the equivalent thereof, for structurally defining the system comprising the macromolecular agent and the polymeric matrix forming material. These steps result in a two-phase system having an interpenetrating phase comprising an agglomerate made of a plurality of clusters of macromolecules that form a network of substantially contiguous particles in the polymeric matrix. The network can be a lightly to highly branched plurality of clusters or it can be a short to long linear chain plurality of clusters. Additionally, it has been found advantageous for achieving the aforesaid defined structure that the loading of the macromolecule in the polymeric matrix be at least 3 parts by weight of the total system as described supra. For example, one suitable method for making the systems comprises blending the monomers, a cross-linking agent and the macromolecular agent, charging the reactants into a mold shaped like a device, and then polymerizing the monomers to yield a polymeric matrix with the interpenetrating macromolecular agent phase therein. Another method for forming the systems consists of dissolving a polymer in an appropriate solvent therefor to form a casting solution, mixing a known amount of the macromolecular agent in the casting solution, charging the solution into a mold, and then drying the mold, usually under vacuum causing the polymer to recrystallize and form the matrix with the interpenetrating macromolecular agent phase therein. The dried polymer is then gently removed from the mold to yield the intended system. Manufacturing procedures are described in *Proc. Nat. Acad. Sci., USA*, Vol. 71, pages 3120 to 3123, 1974; in *Modern Plastic Encyclopedia*, Vol 46, 1969; and in U.S. Pat. No. 3,576,760.

The rate of release of a macromolecule from the systems of this invention can be easily determined by those skilled in the art by using standard procedures. In this manner, particular materials used as the matrix, as well as the macromolecule can be selected, designed and programmed for an intended result. Various techniques that can be used for measuring the amount of a macromolecule for example, a protein or a peptide hormone released from a delivery system includes measuring the amount of protein, or the amount of known constituents produced on degradation of the macromolecules, released by using protein, peptide and amino acid measuring techniques such as the protein determination of Lowry, Sullivan's test for cysteine and cystine, the Hopkins-Cole test for tryptophan, Millan's reaction, the Biuret test, and other tests as disclosed in *J. Biol. Chem.*, Vol 193, pages 265 to 275, 1951; and in Hawk's *Physiological Chemistry*, edited by Oser, B. L., pages 141 to 154, and 176 to 189, 1965, published by McGraw-Hill Co., New York.

EXAMPLES OF THE INVENTION

The following examples are merely illustrative of the present invention and they should not be considered as limiting the scope of the invention in any way, as these examples and other equivalents thereof will become apparent to those versed in the art in the light of the present disclosure, the tables and the accompanying claims.

EXAMPLE 1

A therapeutic two-phase system for the controlled and continuous release of the macromolecule soybean trypsin inhibitor formed as an interpenetrating phase in a polymeric matrix of ethylene-vinyl acetate copolymer having a vinyl acetate content of 40%, was manufactured as follows: first, the ethylene-vinyl acetate copolymer was washed in 2.5% (W/V) reagent quality absolute pure ethyl alcohol at 37° C. in sterile roller bottles. One hundred changes of alcohol were made with a minimum of three hours per wash. After the final wash, the alcohol was decanted and the wet polymer was poured into a sterile glass petri dish. The remaining alcohol was removed by vacuum drying, and the polymer stored until needed.

Next, a polymer casting solution was made by dissolving a measured amount of the above washed ethylene-vinyl acetate copolymer in methylene chloride at 37° C. Then, the soybean trypsin inhibitor was added to 100 to 500 $\mu$l of the casting solution, blended therewith by means of continuous and vigorous agitation, and the resultant placed in a preselected mold. The mold was dried under vacuum overnight causing the copolymer to recrystallize with the interpenetrating trypsin inhibitor phase entrapped therein. The dried system was coated by dipping the pellet in polymer admixed with casting solution. The pellet was then dried under mild vacuum. It was then rehydrated by adding a drop of lactated Ringer's solution and gently removed from the mold. The system releases about 100 nanograms a day of the biochemically active macromolecule into an aqueous environment for a prolonged period exceeding 100 days.

EXAMPLE 2

The procedure of Example 1 was repeated with all the conditions as described except that the macromolecule used to form one system was lysozyme prepared from egg white Grade 1, in another system alkaline phosphatase prepared from chicken intestine mucosa, Type V, and in another system cartilage factor prepared according to the procedure in *Science*, Vol. 193, pages 70 and 71, 1976. These systems released in excess of 100 nanograms a day of the macromolecule into the aqueous media for periods exceeding 100 days.

EXAMPLE 3

The procedures of Examples 1 and 2 were repeated with the added step that for the production of system for in vivo use, the macromolecules were dispersed in 200 $\mu$l of polymer solution, placed in glass petri dishes, dried under vacuum and cut into desired sizes. These sizes were then dipped into pure polymer solution to yield systems having a slower rate of release. Also, slow release systems were made containing lysozyme, alkaline phosphatase and soybean trypsin inhibitor for in vitro use by mixing usually 5 mg of the macromolecule with 100 μl of 10% ethylene-vinyl acetate copolymer having a vinyl acetate content of 40% by weight in methylene chloride, drying under vacuum, and cutting into 1 mm³ systems. These were then coated with a thin film of pure polymer to give systems that released in excess of 100 nanograms a day for periods exceeding 100 days.

EXAMPLE 4

The procedures of the above examples are repeated with all conditions as given, except that the systems are molded into devices for use as subcutaneous implants, uterine systems and ocular implants.

The pharmacological activity of the two-phase systems was ascertained in vivo using the cornea of rabbits. The cornea was used because both its clarity and avascularity permits stereomicroscopic observation of conventional inflammatory characteristics such as edema, white cell infiltration, and neovascularization. These characteristics of inflammation are described in *Am. J. of Path.*, Vol 79, pages 537 to 554, 1975. Inflammation was graded an none, mild or significant. The cornea is the most sensitive of all indicators of inflammation.

Sterile systems, 1.5×1.5×0.5 mm³, were implanted within the corneal lamella of 2 to 3 month old New Zealand while male rabbits by aseptically creating intracorneal pouches according to the procedure disclosed in *J. Nat. Can. Inst.*, Vol 52, pages 413 to 417, 1974. Using a Wheeler cyclodialysis spatula and fine forceps, the implants were placed at the lower edge of the pouch within 1 to 2 mm of the vessels of the corneal, scleral junction. The corneal implants were examined four times weekly over two month periods with a slit lamp stereomicroscope at 6–40× magnification.

The results obtained for systems made of ethylenevinyl acetate copolymer are reported in Table 1, immediately below. The study compared washed and unwashed systems and the results clearly demonstrated that washed systems are compatible with the host and did not cause inflammation in the cornea. In Table 1, the criteria for inflammation were edema, white cells and neovascularization. A response was judged to be mild if any one of the three characteristics was detected, and significant if any one was present in large amounts.

TABLE I
HOST RESPONSE TO CORNEAL IMPLANTED SYSTEMS

| System | Number of tests | Inflammation None | Mild | Significant |
|---|---|---|---|---|
| Ethylene-vinyl acetate copolymer (unwashed) | 20 | 40% | 60% | 0 |
| Ethylene-vinyl acetate copolymer (washed) | 20 | 100% | 0 | 0 |

The amount of macromolecule released from implants was measured using the following in vitro procedure comprising, placing implants in 100×13 mm screw top test tubes containing 2 ml of lactated Ringer's solution, followed by shaking the tubes inside a 4 inch diameter roller bottle rotating at 2 rpm at 37° C., then, at known intervals, removing the implants from their test tube and placing them in new tubes containing fresh Ringer's solution, and finally measuring the amount of protein macromolecules released by the procedure reported in *J. Biol. Chem.* Vol. 193, pages 265 to 275, 1951. Ringer's solution incubated with the polymer matrix free of the interpenetrating phase showed no absorbance when assayed by the above procedure. At the end of all experiments, the systems were analyzed for the amount of unreleased macromolecule therein.

The results of all experiments are expressed as percent of total macromolecule, for example protein, released as a function of time. Total protein was considered the sum of all macromolecules, released and not released. This amount was usually within 20% of the amount, calculated by weight and volumetric measurement, originally present in the system. All the experiments were performed in duplicate or triplicate and means were taken. The average error for any percent reported was ±5%.

The systems were analyzed for slow release of the macromolecular agents biological activity using the agar gel technique described in *Experientia*, Vol. 28, pages 990 to 991, 1972, and in *Anal. Biochem.*, Vol 46, pages 520 to 533, 1972.

The systems were incubated in 20 ml volumes of lactated Ringer's solution at 37° C. The solution was changed 5 times during the first day of incubation, daily each of the next nine days, and every two days during subsequent incubation. Before each change the systems were blotted dry on an absorbent tissue to remove, in part, adherent solution, and then washed with additional Ringer's solution. The systems were removed from incubation periodically, and washed with Ringer's solution, and placed in wells. Order of magnitude titration showed that zones were observed for soybean trypsin inhibitor, lysozyme and alkaline phosphatase released from the polymeric matrix of systems made according to the invention during a 24 hours period in each of the assays, if 100 nanograms or more of biologically active protein was present in a well. Control system that did not contain these proteins did not produce zones when analyzed according to this procedure. The results of a number of tests are summarized in Table 2, immediately below. In Table 2, the three ethylene-vinyl acetate copolymeric systems were prepared according to Example 3, the letters "STI" is an abbreviation for soybean trypsin inhibitor, "L" is for lysozyme and "AP" is for alkaline phosphatase.

TABLE 2
RELEASE TESTS OF BIOCHEMICAL ACTIVITY

| System | Macro-molecules | Concentration of Protein in Protein-Polymer Casting Solution (mg/ml) | Number of Days of Detectable Release |
|---|---|---|---|
| Ethylene-Vinyl Acetate Copolymer | STI | 50 | 100+ |
| Ethylene-Vinyl Acetate Copolymer | L | 50 | 100+ |
| Ethylene-Vinyl Acetate Copolymer | AP | 50 | 100+ |

The release of soybean trypsin inhibitor from ethylene-vinyl acetate copolymer expressed as % of protein released plotted against time expressed in days from ethylene-vinyl acetate copolymer prepared according to Example 3 is shown in FIG. 1. The casting solution used was 10% ethylene-vinyl acetate copolymer. This concentration minimized the initial rate of release from the system and still permitted viscosities low enough so that the solutions were easy to work with.

Figure 2:
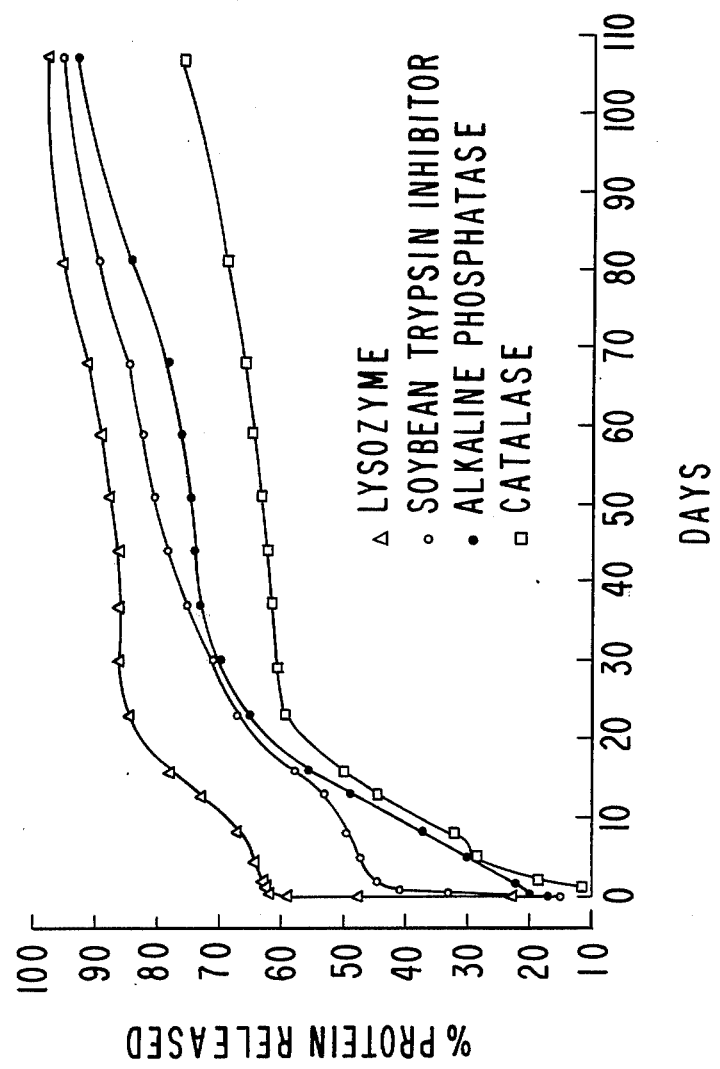

The release rate profiles for four different macromolecules, lysozyme, soybean trypsin inhibitor, alkaline phosphatase and catalase from an ethylene-vinyl acetate copolymer systems prepared according to Example 3 are shown in FIG. 2. The release rates approach zero order kinetics between 20 and 100 days. The protein concentration in all casting solutions was 50 mg/ml.

System comprising ethylene-vinyl acetate copolymer containing tumor angiogenesis factor abbreviated as TAF and which factor is reported in Can. Res., Vol 34, pages 2109 to 2113, 1974, were tested in vivo for their continuous ability to elicit a host vascular response. The systems were prepared according to Example 3, and in over one hundred experiments, implants manufactured as pellets containing TAF were implanted into rabbit corneas and in every case a significant vascular response was observed. No edema or white cells were detected. After releasing TAF in corneas for more than 40 days, several of the polymers were removed and vessels disappeared over a 3-4 week period. When these same polymers were washed in Ringer's solution and transplanted to new corneas, vascular responses were again observed, although rates of vessel growth were somewhat slower than they were in the initial implants. The slow release systems also produced a neovascular response when implanted on a 10 or 11 day old chick CAM. The systems free of TAF induced no such response. The release of TAF from these systems can be used in experiments leading to the development of therapeutic agents indicated as useful for the inhibition of tumor angiogenesis as presented in the above reference.

It is clear from the above that macromolecules with a wide range of molecular weights can be delivered in significant quantities from the systems of this invention and that these systems are compatible with their animal host. The systems can release macromolecules in biochemically and biologically active form for prolonged periods to produce beneficial results. And, while there has been described and pointed out the fundamental novel and useful features of the invention as applied to presently preferred embodiments, those skilled in the art will appreciate that various modifications, changes and omissions can be made in the procedures illustrated and described without departing from the spirit of the invention.

We claim:

1. A therapeutic system for the continuous and controlled administration of insulin, said system being in the form of a body which is sized and shaped for placement in the environment of use, comprising a two-phase composition of:
   (a) a first phase comprising a biocompatible, plastically deformable, hydrophobic matrix having an aqueous fluid sorptivity not greater than 50% by weight, of ethylene-vinyl ester copolymer of the general formula:

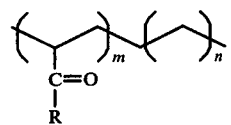

wherein R is a member selected from the group consisting of hydrogen, lower alkyl of 1 to 7 carbons and phenyl, the polymer being insoluble in the environment of use, substantially impermeable to diffusion therethrough of insulin, and containing in admixture therewith;
   (b) a second phase comprising from about 3 to 90 parts by weight of agglomerated particles of insulin.

2. The therapeutic system for the administration of insulin according to claim 1, wherein the insulin is substantially continuous and homogenous with said matrix phase.

3. The therapeutic system for the administration of insulin according to claim 1 wherein the environment is a warm blooded animal.

4. The therapeutic system for the administration of insulin according to claim 1, wherein the aqueous fluid is a member selected from the group consisting of water, saline, buffers and biological fluids.

5. The therapeutic system for the administration of insulin according to claim 1, wherein the system comprises from 3 to 90 parts insulin to 97 to 10 parts of matrix.

6. The therapeutic system for the administration of insulin according to claim 1, wherein the agglomerate comprises a plurality of clusters of insulin molecules that form a network of substantially contiguous particles in the first phase.

7. The therapeutic system for the administration of insulin according to claim 1, wherein the second phase is an interpenetrating phase within the first phase.

8. The therapeutic system for the administration of insulin according to claim 5, wherein the total system contains from 25 to 80 parts by weight of insulin.

9. The therapeutic system for the administration of insulin according to claim 1, wherein the copolymer has a melt index of 0.5 to 100 grams per 10 minutes, a density of 0.920 to 1.00 and a frequency of acyl groups on the ethylene backbone of 1/70 to 1/8.

10. The therapeutic system for the administration of insulin according to claim 1, wherein the polymeric matrix is ethylene-vinyl acetate copolymer.

11. The therapeutic system for the administration of insulin according to claim 1, wherein R is methyl and the copolymer has a fluid sorptivity of from 0.015 to 0.67%.

12. The therapeutic system for the administration of insulin according to claim 1, wherein the two-phase composition is coated with a film of polymer.

* * * * *

UNITED STATES PATENT AND TRADEMARK OFFICE
CERTIFICATE OF CORRECTION

PATENT NO. : 4,164,560
DATED : August 14, 1979
INVENTOR(S) : Moses J. Folkman et al.

It is certified that error appears in the above-identified patent and that said Letters Patent are hereby corrected as shown below:

Column 11, line 20, "in vivo should be underlined.

Column 12, lines 5-10, the structural formula should read as follows:

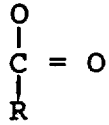

UNITED STATES PATENT AND TRADEMARK OFFICE
CERTIFICATE OF CORRECTION

PATENT NO. : 4,164,560

DATED : August 14, 1979

INVENTOR(S) : Moses J. Folkman et al.

It is certified that error appears in the above-identified patent and that said Letters Patent are hereby corrected as shown below:

Column 3, lines 55-60, the structural formula should read as follows:

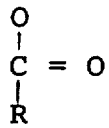

Column 8, line 62, "in vivo" should be underlined.

Column 8-9, line 68 and 1, "in vitro" should be underlined.

Column 9, line 16, "in vivo" should be underlined.

Column 9, line 23, "an" should be --as--.

Column 9, line 27, "while" should be --white--.

Column 10, line 2, "in vitro" should be underlined.

Signed and Sealed this

Fourth Day of December 1979

[SEAL]

Attest:

SIDNEY A. DIAMOND

Attesting Officer

Commissioner of Patents and Trademarks